(12) United States Patent
Han et al.

(10) Patent No.: US 9,773,066 B2
(45) Date of Patent: Sep. 26, 2017

(54) METHODS AND DEVICES FOR COLLECTION AND HEURISTIC ANALYSIS OF LARGE-SCALE BIOGRAPHICAL INFORMATION

(71) Applicant: Dreamsquare Inc., San Jose, CA (US)

(72) Inventors: Shin Hwan Han, Seongnam-si (KR); Sanghyun Park, Fremont, CA (US); Jun Soo Yun, Sunnyvale, CA (US)

(73) Assignee: Dreamsquare Inc., San Jose, CA (US)

( * ) Notice: Subject to any disclaimer, the term of this patent is extended or adjusted under 35 U.S.C. 154(b) by 554 days.

(21) Appl. No.: 14/498,859

(22) Filed: Sep. 26, 2014

(65) Prior Publication Data

US 2016/0092579 A1    Mar. 31, 2016

Related U.S. Application Data

(60) Provisional application No. 62/055,814, filed on Sep. 26, 2014.

(51) Int. Cl.
*G06F 7/58*    (2006.01)
*G06F 17/30*    (2006.01)
*G06F 19/16*    (2011.01)

(52) U.S. Cl.
CPC .... *G06F 17/30867* (2013.01); *G06F 17/3097* (2013.01); *G06F 17/30687* (2013.01); *G06F 19/16* (2013.01)

(58) Field of Classification Search
CPC ....................................... G06F 19/16
USPC ............................................ 703/11
See application file for complete search history.

(56) References Cited

U.S. PATENT DOCUMENTS

| 2012/0078954 A1* | 3/2012 | Araya | G06F 17/30979 707/769 |
| 2016/0092579 A1* | 3/2016 | Han | G06F 17/30867 707/710 |

OTHER PUBLICATIONS

Tim Berners-Lee, The Semantic Web, May 21, 2001.*

* cited by examiner

*Primary Examiner* — Lechi Truong
(74) *Attorney, Agent, or Firm* — Morgan, Lewis & Bockius LLP

(57) ABSTRACT

A computer system crawls a plurality of web pages; parses the crawled information into state events and determines causality between any two of the state events; and stores the state events and the causality in a database. The system receives a first request from a user to determine a path to a target state. The system obtains a current state of the user. The system determines one or more paths from the current state of the user to the target state based on the current state of the user and the state events and the causality, including identifying one or more recommended state events, each recommended state event having a causality value for the target state that satisfies first preselected causality criteria; and provides at least one path from the current state of the user to the target state.

16 Claims, 14 Drawing Sheets

|         | Goal 1 | Goal 2 | Goal 3 | Goal 4 | Goal 5 | Goal 6 | Goal 7 |
|---------|--------|--------|--------|--------|--------|--------|--------|
| User 1  | ○      |        |        |        |        |        |        |
| User 2  | ○      | ○      |        |        |        |        |        |
| User 3  | ○      | ○      |        | ○      |        |        |        |
| User 4  | ○      | ○      |        | ○      | ○      |        |        |
| User 5  | ○      | ○      | ○      | ○      | ○      |        | ○      |
| User 6  | ○      | ○      |        | ○      |        | ○      | ○      |
| User 7  | ○      | ○      |        | ○      | ○      | ○      | ○      |
| Ratio   | 7/7    | 6/7    | 1/7    | 5/7    | 4/7    | 2/7    | 3/7    |

FIGURE 4A

|         | Goal 1 | Goal 2 | Goal 3 | Goal 4 | Goal 5 | Goal 6 | Goal 7 | Effects |
|---------|--------|--------|--------|--------|--------|--------|--------|---------|
| Goal 1  | N/A    | 24     | 4      | 78     | 10     | 32     | 5      | 153     |
| Goal 2  | 12     | N/A    | 48     | 4      | 23     | 29     | 2      | 118     |
| Goal 3  | 23     | 9      | N/A    | 1      | 89     | 5      | 17     | 144     |
| Goal 4  | 12     | 44     | 0      | N/A    | 70     | 9      | 22     | 157     |
| Goal 5  | 87     | 2      | 35     | 70     | N/A    | 14     | 80     | 288     |
| Goal 6  | 15     | 47     | 29     | 29     | 23     | N/A    | 20     | 163     |
| Goal 7  | 19     | 3      | 9      | 16     | 1      | 3      | N/A    | 51      |
| Causes  | 168    | 129    | 125    | 198    | 216    | 92     | 146    | Sum     |

FIGURE 4B

| | Goal 1 | Goal 2 | Goal 3 | Goal 4 | Goal 5 | Goal 6 | Goal 7 | Effects |
|---|---|---|---|---|---|---|---|---|
| Goal 1 | N/A | 24 | 4 | 78 | 10 | 32 | 5 | 153 |
| Goal 2 | 12 | N/A | 48 | 4 | 23 | 29 | 2 | 106 |
| Goal 3 | 23 | 9 | N/A | 1 | 89 | 5 | 17 | 112 |
| Goal 4 | 12 | 44 | 0 | N/A | 70 | 9 | 22 | 101 |
| Goal 5 | 87 | 2 | 35 | 70 | N/A | 14 | 80 | 94 |
| Goal 6 | 15 | 47 | 29 | 29 | 23 | N/A | 20 | 20 |
| Goal 7 | 19 | 3 | 9 | 16 | 1 | 3 | N/A | 51 |
| Causes | 168 | 105 | 73 | 115 | 24 | 3 | 146 | |

FIGURE 4C

| | Goal 1 | Goal 2 | Goal 3 | Goal 4 | Goal 5 | Goal 6 | Goal 7 | Effects |
|---|---|---|---|---|---|---|---|---|
| Goal 1 | N/A | 24 | 4 | 78 | 10 | 32 | 5 | 153 |
| Goal 2 | 12 | N/A | 48 | 4 | 23 | 29 | 2 | 106 |
| Goal 3 | 23 | 9 | N/A | 1 | 89 | 5 | 17 | 112 |
| Goal 4 | 12 | 44 | 0 | N/A | 70 | 9 | 22 | 101 |
| Goal 5 | 87 | 2 | 35 | 70 | N/A | 14 | 80 | 94 |
| Goal 6 | 15 | 47 | 29 | 29 | 23 | N/A | 20 | 20 |
| Goal 7 | 19 | 3 | 9 | 16 | 1 | 3 | N/A | 51 |
| Causes | 168 | 105 | 73 | 115 | 24 | 3 | 146 | Events Sum |

FIGURE 4D

| | Goal 1 | Goal 2 | Goal 3 | Goal 4 | Goal 5 | Goal 6 | Goal 7 | Sum |
|---|---|---|---|---|---|---|---|---|
| User 1 | 100% | 78% | 50% | 90% | 51% | 100% | 90% | 559% |
| User 2 | 98% | 50% | 89% | 0% | 51% | 69% | 71% | 428% |
| User 3 | 99% | 50% | 50% | 100% | 50% | 57% | 0% | 406% |
| User 4 | 50% | 100% | 100% | 95% | 100% | 50% | 89% | 582% |
| User 5 | 0% | 100% | 67% | 100% | 100% | 98% | 90% | 555% |
| User 6 | 53% | 89% | 0% | 90% | 57% | 56% | 50% | 395% |
| User 7 | 78% | 69% | 0% | 50% | 100% | 92% | 0% | 389% |
| The closest | User 3 | User 7 | User 3 | User 6 | User 2 | User 5 | User 5 | User 5 |

FIGURE 4E

|  | Goal 1 | Goal 2 | Goal 3 | Goal 4 | Goal 5 | Goal 6 | Goal 7 | Sum |
|---|---|---|---|---|---|---|---|---|
| User 1 | 100% | 78% | 50% | 90% | 51% | 100% | 90% | 559% |
| User 2 | 98% | 50% | 89% | 0% | 51% | 69% | 71% | 428% |
| User 3 | 99% | 50% | 50% | 100% | 50% | 57% | 0% | 406% |
| User 4 | 50% | 100% | 100% | 93% | 100% | 50% | 89% | 582% |
| User 5 | 0% | 100% | 67% | 100% | 100% | 99% | 90% | 556% |
| User 6 | 53% | 89% | 0% | 90% | 57% | 56% | 50% | 395% |
| User 7 | 78% | 69% | 0% | 50% | 100% | 92% | 0% | 349% |
| The highest | User 2 | User 4,5 | User 4 | User 3,5 | User 4,5,7 | User 5 | User 5 | User 4 |

FIGURE 4F

In response to receiving the first request

516 The one or more recommended state events are one or more N-generation recommended state events. Repeat identifying one or more recommended state events so that one or more N-1 generation recommended state events are identified for at least one N generation recommended state event. Each N-1 generation recommended state event has a causality value for the one N generation recommended state event that satisfies the first preselected causality criteria. N is reduced by a generation each time the identifying is repeated.

518 Identify one or more synergy state events. Each synergy state event of the one or more synergy state events has a relative frequency that satisfies preselected frequency criteria. The relative frequency is based on respective frequencies of transitions to the target state event from multiple state events, that have transitions to the target state event, including the synergy state event.

520 Determine a probability of achieving the target state from the current state of the user 522 Determine the probability of achieving the target state from the current state of the user based on relative frequencies of the one or more synergy events

FIGURE 5B

524 Subsequent to storing the state events and the causality in the database, receive a second request to recommend one or more target states. In response to receiving the second request, obtain the current state of the user, wherein the current state of the user includes one or more state events associated with the user; determine one or more target states based on the current state of the user and the state events and the causality stored in the database, including identifying one or more probable state events, each probable state event of the one or more probable state events having a causality value from the current state of the user that satisfies second preselected causality criteria; and provide at least a subset of the one or more target states.

526 The one or more probable state events are one or more M-generation probable state events. Repeat identifying one or more probable state events so that one or more M+1 generation probable state events are identified for at least one M generation probable state event. Each M+1 generation probable state event has a causality value for the one M generation probable state event that satisfies the second preselected causality criteria. M is advanced by a generation each time the identifying is repeated.

FIGURE 5C

528 Subsequent to storing the state events and the causality in the database, receive a third request to identify one or more users. In response to receiving the third request, identify one or more target state events of the user; and identify one or more candidate users who are distinct from the user. Each candidate user of the one or more candidate users is associated with at least one target state event of the one or more target state events associated with the user. Identify at least a subset of the one or more candidate users based on preselected user selection criteria; and provide at least the subset of the one or more candidate users identified based on the preselected user selection criteria.

530 The preselected user selection criteria require that a probability of achieving a target state event, of the one or more target state events of the user, for a candidate user is higher than a probability of achieving the target state event for any other candidate user of the one or more candidate users 532 The preselected user selection criteria require that a sum of respective probabilities of achieving respective target state events, of the one or more target state events of the user, for a candidate user is higher than a sum of respective probabilities of achieving respective target state events for any other candidate user of the one or more candidate users 534 The preselected user selection criteria require that all of the one or more target state events of the user are associated with a candidate user as target state events of the candidate user 536 The preselected user selection criteria require that a sum of respective probabilities of achieving respective target state events, of the one or more target state events of the user, by a candidate user is closer to a sum of respective probabilities of achieving the respective target state events by the user than any other candidate user of the one or more candidate users

FIGURE 5D

538 Subsequent to storing the state events and the causality in the database, receive a fourth request to recommend one or more target state events. In response to receiving the fourth request, identify one or more state events of the user, and identify a plurality of related users. Each related user has at least one state event of the one or more state events of the user. Identify one or more recommended state events of the plurality of related users. Each recommended state event of the one or more recommended state events is not associated with the user. Identify at least a subset of the one or more recommended state events of the plurality of related users based on preselected recommended state event criteria; and provide at least the subset of the one or more recommended state events of the plurality of related users.

540 Subsequent to storing the state events and the causality in the database, receive a fifth request to identify one or more past states. In response to receiving the fifth request, obtain the current state of the user. The current state of the user includes one or more state events associated with the user. Determine one or more past states based on the current state of the user and the state events and the causality stored in the database, including identifying one or more probable past state events, each probable past state event of the one or more probable past state events having a causality value to the current state of the user that satisfies third preselected causality criteria. Provide at least a subset of the one or more past states.

542 The one or more probable past state events are one or more P-generation probable past state events. Repeat identifying one or more probable past state events so that one or more P-1 generation probable past state events are identified for at least one P generation probable past state event. Each P-1 generation probable past state event has a causality value to the one P generation probable past state event that satisfies the third preselected causality criteria. P is reduced by a generation each time the identifying is repeated.

FIGURE 5E

METHODS AND DEVICES FOR COLLECTION AND HEURISTIC ANALYSIS OF LARGE-SCALE BIOGRAPHICAL INFORMATION

RELATED APPLICATION

This application claims priority to U.S. Provisional Patent Application Ser. No. 62/055,814, filed Sep. 26, 2014, which is incorporated by reference herein in its entirety.

TECHNICAL FIELD

This application relates generally to analysis of biographical information, and in particular, to computer systems and methods for heuristic analysis of large-scale (also called herein "big data") biographical information.

BACKGROUND

Career planning and management are gaining significant interests, and many scientific tools have been developed and used to assist career planning and management. However, existing tools rely on simplistic categorization of career paths, and thus, are not sufficiently accurate for each individual's background and goals.

SUMMARY

Accordingly, there is a need for more effective and accurate methods and systems for collecting and analyzing large-scale biographical information. Such methods and systems optionally complement or replace conventional methods for collecting and analyzing biographical information.

In accordance with some embodiments, a method is performed at a computer system with one or more processors and memory. The method includes crawling a plurality of web pages, a respective web page containing biographical information of a respective person; parsing the crawled information into state events and determining causality between any two of the state events; storing the state events and the causality in a database; and, subsequent to storing the state events and the causality in the database, receiving a first request from a user to determine a path to a target state. The target state includes a target state event. The method also includes, in response to receiving the first request, obtaining a current state of the user. The current state of the user includes one or more state events associated with the user. The method further includes, determining one or more paths from the current state of the user to the target state based on the current state of the user and the state events and the causality stored in the database, including identifying one or more recommended state events, each recommended state event of the one or more recommended state events having a causality value for the target state that satisfies first preselected causality criteria; and providing at least one path from the current state of the user to the target state.

In accordance with some embodiments, a computer system includes one or more processors; and memory storing one or more programs for execution by the one or more processors. The one or more programs including instructions for performing the method described above. In accordance with some embodiments, a computer readable storage medium stores one or more programs for execution by one or more processors of a computer system. The one or more programs including instructions for performing the method described above.

Thus, computer systems with large databases of biographical information are provided with more effective methods for collecting and analyzing the biographical information, thereby increasing the effectiveness and user satisfaction with such computer systems. Such methods may complement or replace conventional methods for collecting and analyzing biographical information.

BRIEF DESCRIPTION OF THE DRAWINGS

For a better understanding of the disclosed embodiments, reference should be made to the Description of Embodiments below, in conjunction with the following drawings in which like reference numerals refer to corresponding parts throughout the figures.

FIGS. 4A-4F illustrate state event data used for analyzing biographical information in accordance with some embodiments.

FIG. 5A-5E are flow diagrams illustrating a method of identifying recommended state events in accordance with some embodiments.

DESCRIPTION OF EMBODIMENTS

Figure 1:
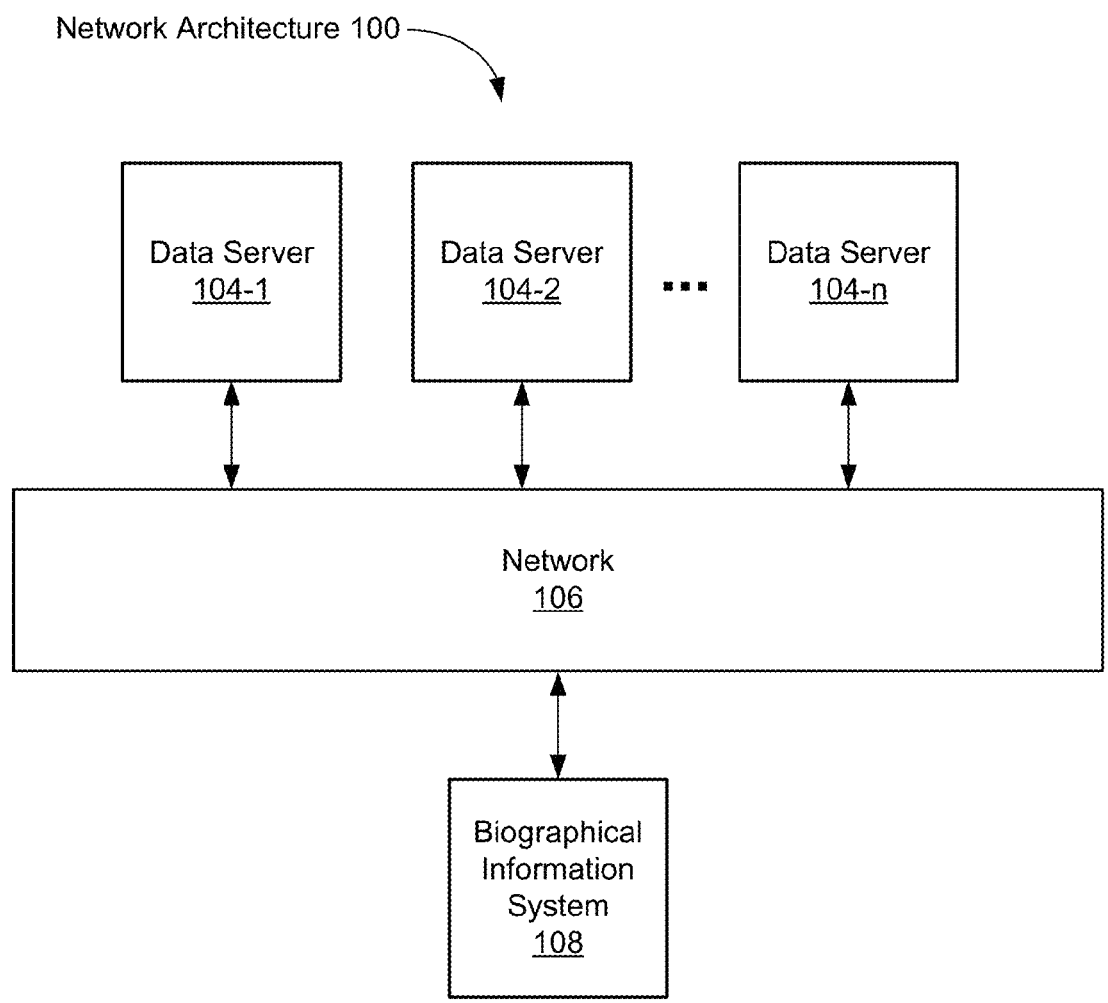
FIG. 1 is a block diagram illustrating an exemplary network architecture of a biographical information system in accordance with some embodiments.

Career planning and management are gaining significant interests, and many scientific tools have been developed and used to assist career planning and management. However, existing tools rely on simplistic categorization of career paths, and thus, are not sufficiently accurate for each individual's background and goals.

With the advancements in communications technologies, and in particular, with the advancements in the Internet technologies, a significant amount of information, which was not imaginable previously, has become available. In particular, people's biographical information (e.g., work history and educational background) can be easily located on the Internet. However, systems and devices for utilizing such information have not been available.

As described below, a computer system collects biographical information by crawling websites (and their web pages), parses the biographical information into milestones (called state events) and determines their connections, and stores the milestones and their connections in a database. The database is analyzed by various methods to provide career advice (e.g., recommending a path to a career goal, recommending new career goals, predicting a person's future milestones, and identifying potential mentors).

Because "big data" of biographical information and heuristics based on such "big data" are used, the computer system is capable of providing more effective and accurate recommendations.

Reference will now be made to embodiments, examples of which are illustrated in the accompanying drawings. In the following description, numerous specific details are set forth in order to provide an understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

It will also be understood that, although the terms first, second, etc. are, in some instances, used herein to describe various elements, these elements should not be limited by these terms. These terms are used only to distinguish one element from another. For example, a first user interface could be termed a second user interface, and, similarly, a second user interface could be termed a first user interface, without departing from the scope of the various described embodiments. The first user interface and the second user interface are both user interfaces, but they are not the same user interface.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is, optionally, construed to mean "when" or "upon" or "in response to determining" or "in response to detecting" or "in accordance with a determination that," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]" or "in accordance with a determination that [a stated condition or event] is detected," depending on the context.

FIG. 1 is a block diagram illustrating an exemplary network architecture of a biographical information system in accordance with some embodiments. The network architecture 100 includes a number of data servers 104-1, 104-2, . . . 104-n and a number of client devices (also called "client systems," "client computers," or "clients") (not shown) communicably connected to a biographical information system 108 by one or more networks 106.

In some embodiments, the client devices are computing devices, such as laptops and desktop computers, or other appropriate computing devices that can be used to communicate with an electronic biographical information system.

In some embodiments, the data servers 104-1, 104-2, . . . 104-n are electronic server systems (e.g., web servers, etc.) configured for providing biographical data.

In some embodiments, the biographical information system 108 is a single computing device, such as a computer server, while in other embodiments, the biographical information system 108 is implemented by multiple computing devices working together to perform the actions of a server system (e.g., cloud computing).

In some embodiments, the network 106 is a public communication network (e.g., the Internet or a cellular data network), a private communications network (e.g., private LAN or leased lines), or a combination of such communication networks.

In some embodiments, the biographical information system 108 crawls web pages provided by the data servers 104-1 through 104-n and stores crawled information. Further details are provided below with respect to FIG. 2 and FIGS. 5A-5E.

Figure 2:
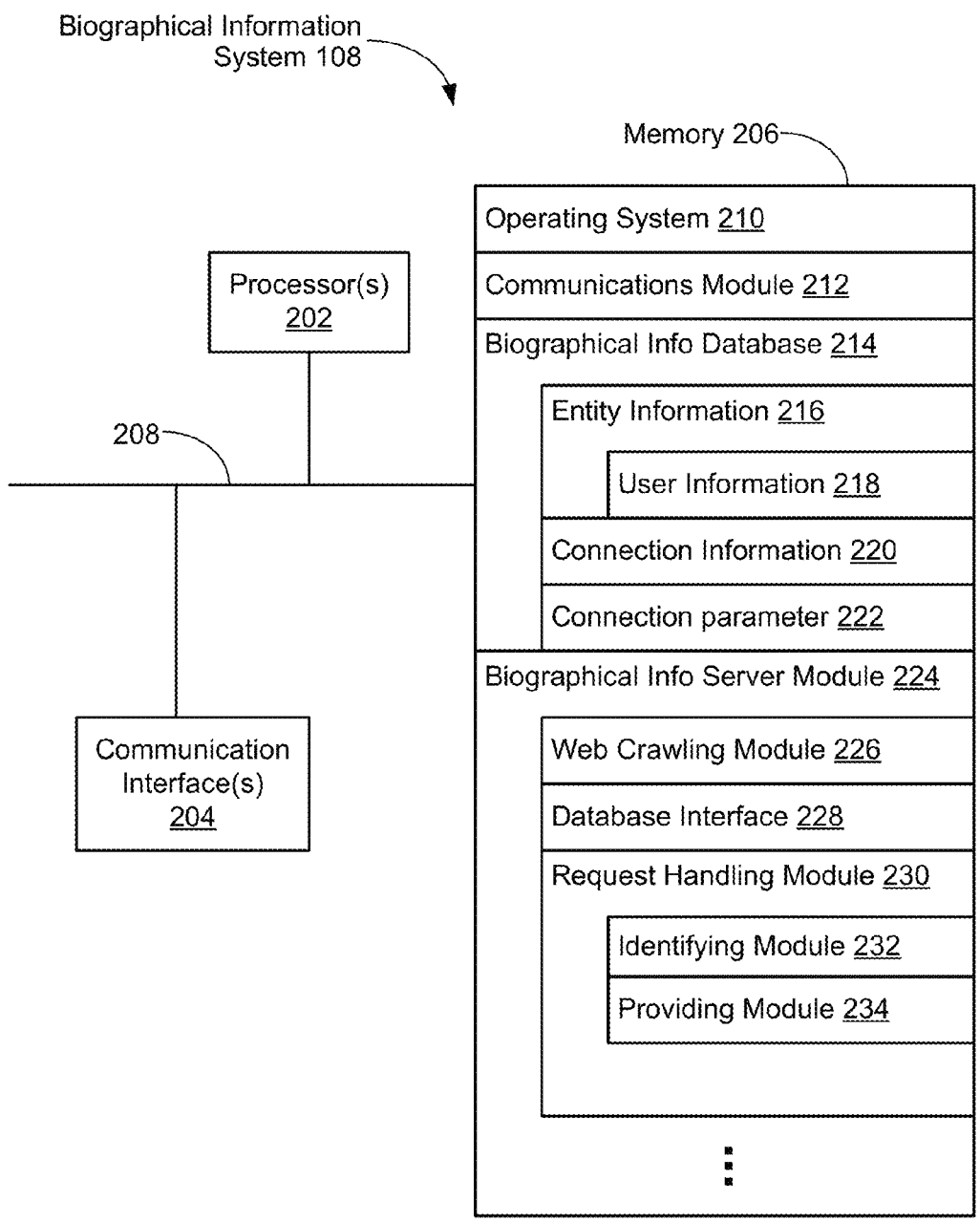
FIG. 2 is a block diagram illustrating an exemplary biographical information system in accordance with some embodiments.

FIG. 2 is a block diagram illustrating an exemplary biographical information system 108 in accordance with some embodiments. The biographical information system 108 typically includes one or more processing units (processors or cores) 202, one or more network or other communications interfaces 204, memory 206, and one or more communication buses 208 for interconnecting these components. The communication buses 208 optionally include circuitry (sometimes called a chipset) that interconnects and controls communications between system components. The biographical information system 108 optionally includes a user interface (not shown). The user interface, if provided, may include a display device and optionally includes inputs such as a keyboard, mouse, trackpad, and/or input buttons. Alternatively or in addition, the display device includes a touch-sensitive surface, in which case the display is a touch-sensitive display.

Memory 206 includes high-speed random access memory, such as DRAM, SRAM, DDR RAM, or other random access solid state memory devices; and may include non-volatile memory, such as one or more magnetic disk storage devices, optical disk storage devices, flash memory devices, or other non-volatile solid state storage devices. Memory 206 may optionally include one or more storage devices remotely located from the processor(s) 202. Memory 206, or alternately the non-volatile memory device(s) within memory 206, includes a non-transitory computer readable storage medium. In some embodiments, memory 206 or the computer readable storage medium of memory 206 stores the following programs, modules and data structures, or a subset or superset thereof:

- an operating system 210 that includes procedures for handling various basic system services and for performing hardware dependent tasks;
- a network communication module 212 that is used for connecting the biographical information system 108 to other computers via the one or more communication network interfaces 204 (wired or wireless) and one or more communication networks, such as the Internet, cellular telephone networks, mobile data networks, other wide area networks, local area networks, metropolitan area networks, and so on;
- a biographical information database 214 for storing data associated with biographical information, such as:
  - entity information 216, which optionally includes user information 218;
  - connection information 220; and
  - connection parameter 222; and
- a biographical information server module 224, including:
  - a web crawling module 226 for crawling web pages;
  - a database interface 228, which assists reading data from, and storing data into, a database, such as the biographical information database 214; and
  - a request handling module 230 for receiving and processing requests (e.g., requests from a client device), including:

identifying module 232 for identifying one or more state events; and providing module 234 for outputting results (e.g., sending results to a client device).

The biographical information database 214 stores entity information 216 (e.g., people's education and work experience) in one or more types of databases, such as graph, dimensional, flat, hierarchical, network, object-oriented, relational, and/or XML databases.

In some embodiments, the biographical information database 214 includes a graph database, with entity information 216 represented as nodes in the graph database and connection information 220 represented as edges in the graph database. The graph database includes a plurality of nodes, as well as a plurality of edges that define connections between corresponding nodes. In some embodiments, the nodes and/or edges themselves are data objects that include the identifiers, attributes, and information for their corresponding entities. In some embodiments, the nodes also include pointers or references to other objects, data structures, or resources for use in rendering content in conjunction with the rendering of the pages corresponding to the respective nodes at clients 104.

In some embodiments, entity information 216 includes user information 218, such as user profiles, login information, privacy and other preferences, biographical data, and the like. In some embodiments, for a given user, the user information 218 includes the user's name, anonymized identifier, employment history, education background, target state events (e.g., goals), interests, and/or other information.

In some embodiments, connection information 220 includes information about the relationships between entities in the biographical information database 214. In some embodiments, connection information 220 includes information about edges that connect pairs of nodes in a graph database. In some embodiments, an edge connecting a pair of nodes represents a relationship between the pair of nodes.

In some embodiments, connection parameter 222 includes causality values (e.g., transition parameters).

Each of the above identified modules and applications correspond to a set of executable instructions for performing one or more functions described above and the methods described in this application (e.g., the computer-implemented methods and other information processing methods described herein). These modules (i.e., sets of instructions) need not be implemented as separate software programs, procedures or modules, and thus various subsets of these modules are, optionally, combined or otherwise re-arranged in various embodiments. In some embodiments, memory 206 stores a subset of the modules and data structures identified above. Furthermore, memory 206 optionally stores additional modules and data structures not described above.

Figure 3:
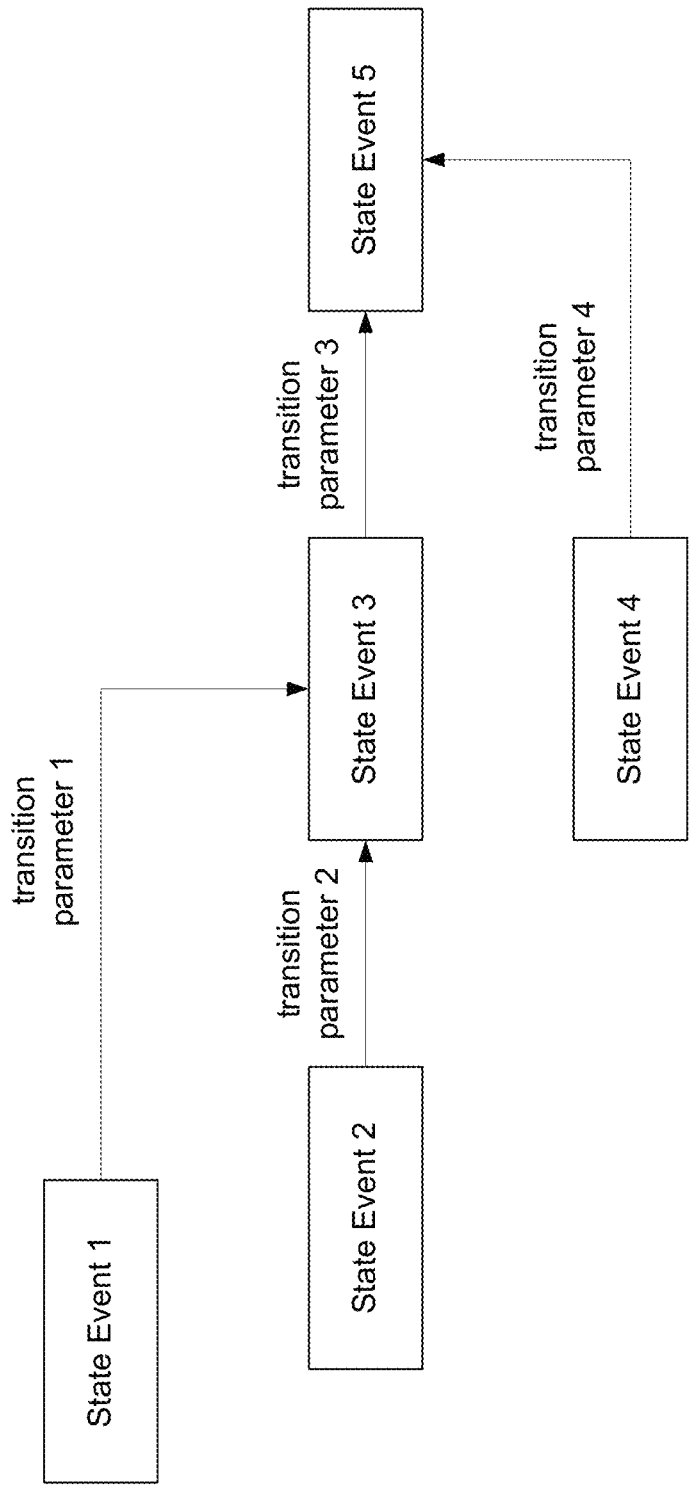
FIG. 3 is a block diagram illustrating relationships among state events in accordance with some embodiments.
Figure 5A:
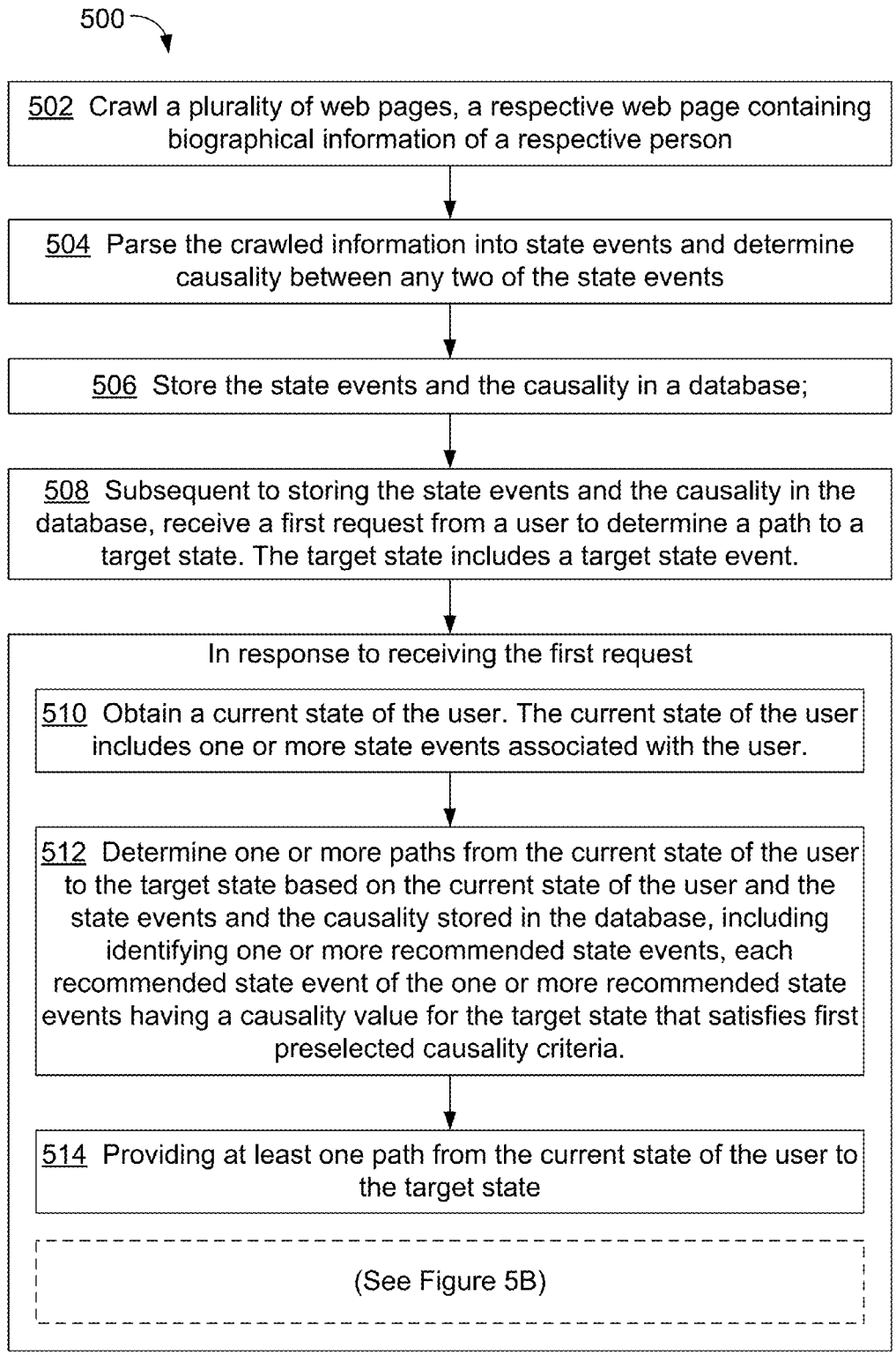

FIG. 3 is a block diagram illustrating relationships among state events in accordance with some embodiments.

In FIG. 3, multiple state events are shown (e.g., State Event 1 through State Event 5). In some embodiments, each state event corresponds to a biographical event (e.g., having a particular job, receiving a particular degree from a school, achieving a career milestone, etc.). In one example, State Event 1 represents receiving a college degree in computer sciences from a particular school, State Event 2 represents (having worked as) an intern at a particular company, State Event 3 represents (having worked as) a software engineer at the particular company, State Event 4 represents completing a management course, and State Event 5 represents (having worked as or working as) a manager at the particular company.

In FIG. 3, State Event 1 is connected with State Event 3. As indicated with a direction of an arrow, State Event 1 has causality to State Event 3, and State Event 3 has causality from State Event 1. Similarly, State Event 2 is connected with State Event 3. Thus, State Event 2 has causality to State Event 3, and State Event 3 has causality from State Event 2. In some embodiments, state events do not need to be directly connected to have causality. For example, State Event 1 has causality to State Event 5 in some embodiments.

In some embodiments, each connection is associated with a causality value (also called herein a transition parameter). FIG. 3 includes multiple transition parameters (e.g., transition parameter 1 through transition parameter 5). In some embodiments, a transition parameter represents a probability of transition. For example, Transition Parameter 1 represents a probability of someone at State Event 1 (having a college degree in computer sciences from a particular school) getting to State Event 3 (becoming a software engineer at the particular company). Transition Parameter 2 represents a probability of someone at State Event 2 (having worked as an intern at the particular company) getting to State Event 3 (becoming a software engineer at the particular company). Transition Parameter 3 represents a probability of someone at State Event 3 (working as a software engineer at the particular company) getting to State Event 5 (becoming a manager at the particular company). Transition Parameter 4 represents a probability of someone at State Event 4 (completing a management class) getting to State Event 5 (becoming a manager at the particular company). In some embodiments, the probability of transition is represented in percentile.

Such state events and their relationships can be obtained from various sources, such as resumes, social network postings, and government websites. In some embodiments, such events and their relationships (e.g., transition parameters) are stored in a database (e.g., a big data database). For example, web pages that include biographical information are collected by crawling, biographical information in the crawled web pages is parsed into state events, and the parsed state events and their relationships are stored in a database. Using data obtained from a large number of web pages (e.g., thousands, tens of thousands, hundreds of thousands, millions, or tens of millions web pages), statistical analysis of the biographical information provides more effective and accurate results.

FIGS. 4A-4F illustrate state event data used for analyzing biographical information in accordance with some embodiments.

FIG. 4A illustrates state event data used in recommending one or more target state events in accordance with some embodiments.

The table shown in FIG. 4A includes multiple users (e.g., user 1 through user 7) in respective rows and multiple target state events (also called herein goals) (e.g., goal 1 through goal 7) in respective columns. User 1 has only one target state event, namely goal 1. In response to recommend one or more target state events for user 1, other users who also have goal 1 as a target state event are identified (e.g., user 2 through user 7), and target state events of the identified users are obtained (e.g., goal 2 through goal 7). From goal 2 through goal 7, goal 2 is a most popular goal among the identified users (e.g., all six users have goal 2 as a target state event). Thus, goal 2 can be recommended as a target state event to user 1. In some embodiments, multiple target state events are identified based on popularity criteria (e.g., top three most popular target state events, target state events that more than 50% of other users have, etc.). In some embodiments, a least popular target state event is recommended (e.g., goal 3).

FIG. 4B illustrates state event data used in identifying synergy state events in accordance with some embodiments.

The table shown in FIG. 4B includes multiple state events (e.g., goal 1 through goal 7) as causes in respective rows and the same state events as effects in respective columns. Each number in a box corresponding to a cause state event and an effect state event represents a frequency of transitions observed from biographical information of a large of people. For example, twelve people who achieved goal 2 subsequently achieved goal 1, twenty three people who achieved goal 3 subsequently achieved goal 1, seventy people who achieved goal 5 subsequently achieved goal 4.

Thus, for a person who wants to achieve goal 1, the table shown in FIG. 4B can be used to identify which other goals are helpful for achieving goal 1. For example, goal 5 is the most frequent cause for achieving goal 1, having eighty seven cases, and goal 2 is the least frequent cause for achieving goal 1, having only twelve cases. Alternatively, a relative importance of each other goal in achieving a particular goal can be expressed in a fraction or in percentile (e.g., a frequency divided by a sum of frequencies for a particular effect state event). For example, the synergy effect of goal 2 in achieving goal 1 can be described as 7.1% (≈12/168), and the synergy effect of goal 5 in achieving goal 1 can be described as 51.8% (≈87/168).

FIG. 4C illustrates state event data used in identifying recommended state events in accordance with some embodiments.

The table shown in FIG. 4C is similar to the table shown in FIG. 4B. From the table shown in FIG. 4C, it can be identified that, for achieving goal 1, goal 5 is the most frequent cause state event (e.g., many people who achieved goal 5 subsequently achieved goal 1). In addition, it can be identified from the table in FIG. 4C that, for achieving goal 5, goal 3 is the most frequent cause state event (e.g., many people who achieved goal 3 subsequently achieved goal 5). Similarly, goal 2 is the most frequent cause state event for goal 3, goal 6 is the most frequent cause state event for goal 2. Thus, a recommended path for achieving goal 1 starts from goal 6, followed by goal 2, goal, 3, goal 5, and goal 1.

FIG. 4D illustrates state event data used in identifying one or more probable state events in accordance with some embodiments.

The table shown in FIG. 4D is similar to the tables shown in FIGS. 4B and 4C. From the table shown in FIG. 4D, it is identified that a person having achieved goal 3 is most likely to achieve goal 5. In addition, from the table shown in FIG. 4D, it is identified that a person having achieved goal 5 is most likely to achieve goal 1. Thus, goals 1 and 5 are identified as probable state events for the person having achieved goal 3.

FIG. 4E illustrates state event data used in recommending one or more users in accordance with some embodiments.

The table shown in FIG. 4E includes multiple users (e.g., user 1 through user 7) in respective rows and multiple goals (e.g., goal 1 through goal 7) in respective columns. Each number in a box corresponding to a user row and a goal column represents how much progress a corresponding has made for achieving a corresponding goal. For example, user 1 has achieved goal 1 (represented by 100%), made 78% progress in achieving goal 2, 50% progress in achieving goal 3, etc. User 2 through user 7 are other users who also have goals that user 1 has (e.g., goal 1 through goal 7). Similarly, the progress that each other use has made for achieving the listed goals is indicated with numbers. In some embodiments, a sum of all the progress numbers for each user is used to identify recommended users. For example, user 1 has the sum of 559%. User 5 has a sum of 555%, which is a sum that is the closest to the sum of user 5, among the listed sums. Thus, user 5 is recommended to user 1 (e.g., as a study companion, etc.).

FIG. 4F illustrates state event data used in identifying one or more users in accordance with some embodiments.

The table shown in FIG. 4F is similar the table shown in FIG. 4E. From the table shown in FIG. 4F, user 4 has the highest sum. Thus, user 4 is deemed to have made the most progress for the goals that user 1 has achieved or wants to achieve, and user 4 is recommended to user 1 (e.g., as a mentor, etc.).

FIG. 5A-5E are flow diagrams illustrating a method 500 of identifying recommended state events in accordance with some embodiments.

The method 500 is performed at a computer system (e.g., biographical information system 108, FIG. 2) with one or more processors and memory.

The system crawls (502) a plurality of web pages, a respective web page containing biographical information of a respective person. In some embodiments, crawling a plurality of web pages includes retrieving and storing the plurality of web pages (e.g., from data servers 104, FIG. 1). In some embodiments, the system crawls multiple web pages concurrently. For example, the biographical information system 108 in FIG. 1 may retrieve one or more pages from data server 104-1 while retrieving one or more pages from data server 104-2. In some embodiments, the biographical information system 108 includes dozens of servers for crawling the plurality of web pages.

The system parses (504) the crawled information into state events and determines causality between any two of the state events. For example, the system extracts educational background (e.g., educational institution, degree, and period) and/or work history (e.g., employer, title, and period) from an online biography (e.g., a LinkedIn or Facebook web page, etc.). In some embodiments, the system parses the crawled information into state events using one or more templates (e.g., a template for a LinkedIn web page). In some embodiments, the system determines a sequence of the state events, and determines causality based on the sequence of the state events. For example, in some embodiments, a first state event (also called herein a preceding state event) that precedes a second state event (also called herein a following state event) is deemed to be a cause of the second state event.

The system stores (506) the state events and the causality in a database (e.g., biographical information database 214, FIG. 2). For example, the system stores the state events in the entity information 216 and the causality in the connection information 220. In some embodiments, the system stores the state events and the causality so that the state events and the causality from one web page are aggregated with state events and causality from multiple other web pages. In some embodiments, the system stores the state events and the causality so that the state events and the causality determined from one web page can be identified separately from state events and causality determined from other web pages.

In some embodiments, the system determines connection parameters (e.g., transition parameters) based on the state events and the causality. For example, the system may count a number of transitions from State Event 1 to State Event 3 for all or a subset of data stored in the database (e.g., how many people who received a college degree in computer sciences from a particular school got a job as a software engineer at a particular company). In some embodiments, only a subset of data is used for determining the connection parameters (e.g., recent ten-year data).

Subsequent to storing the state events and the causality in the database, the system receives (508) a first request from a user to determine a path to a target state. In some embodiments, the request is sent from a client device (e.g., a laptop or a desktop) associated with the user. For example, the user may access the system using a web browser on the client device, and submit a request to determine a path to a target state (e.g., how can I become a CEO of this company?). The target state includes a target state event (e.g., a particular position at a particular company or a particular degree from a particular school).

In response to receiving the first request, the system obtains (510) a current state of the user. The current state of the user includes one or more state events associated with the user. For example, the user may submit his or her current states to the system so that the system can perform the requested operation based on the user's current states. In some embodiments, the current states represent educational background and work history to date (e.g., having received a college degree in a particular subject matter from a particular school).

The system determines (512) one or more paths from the current state of the user to the target state based on the current state of the user and the state events and the causality stored in the database, including identifying one or more recommended state events, each recommended state event of the one or more recommended state events having a causality value for the target state that satisfies first preselected causality criteria. For example, as shown in FIG. 4C, for achieving a particular goal (e.g., goal 1), goal 5 is recommended, because there are many precedents that people who have achieved goal 5 subsequently achieve goal 1. In addition, goal 3 may be also recommended, because there are many precedents that people who have achieved goal 3 subsequently achieve goal 5. In some embodiments, the first preselected causality criteria are satisfied when a recommended state event has a higher causality value than any other state event. For example, for achieving goal 1, goal 5 has the highest causality value among goal 2 through goal 7. In some embodiments, the first preselected causality criteria are satisfied when a causality value exceeds a preselected threshold (e.g., a frequency of 50 or an average of frequencies, etc.).

The system provides (514) at least one path from the current state of the user to the target state. For example, the system sends a web page that includes the one or more recommended state events to the client device associated with the user for display. In some embodiments, the at least one path includes the one or more recommended state events (e.g., "since you have achieved goal 2, you need to achieve goal 3 next and then goal 5 to achieve goal 1").

In some embodiments, in response to receiving the first request, the system determines one or more paths to the target state based on the state events and the causality stored in the database, regardless of the current state of the user. Determining the one or more paths includes identifying one or more recommended state events, each recommended state event of the one or more recommended state events having a causality value for the target state that satisfies the first preselected causality criteria. The system provides at least one path to the target state.

In some embodiments, the one or more recommended state events are (516, FIG. 5B) one or more N-generation recommended state events. For example, goal 5 is an N generation recommended state event (e.g., −1 generation). The system repeats identifying one or more recommended state events so that one or more N−1 generation recommended state events are identified for at least one N generation recommended state event. For example, goal 3 is identified as an N−1 generation recommended state event (e.g., −2 generation). Each N−1 generation recommended state event has a causality value for the one N generation recommended state event that satisfies the first preselected causality criteria and N is reduced by a generation each time the identifying is repeated (e.g., −3 generation recommended state events are identified subsequently).

In some embodiments, the system identifies (518) one or more synergy state events. Each synergy state event of the one or more synergy state events has a relative frequency that satisfies preselected frequency criteria. The relative frequency is based on respective frequencies of transitions to the target state event from multiple state events, that have transitions to the target state event, including the synergy state event. In some embodiments, the relative frequency for a respective cause state event is a ratio between a respective frequency for a transition from the respective cause state event to the target state event and a sum of frequencies for transitions from all cause state events to the target state event. For example, as shown in FIG. 4B, a transition from goal 5 to goal 1 has a relative frequency of 51.8% (≈87/168) and a transition from goal 2 to goal 1 has a relative frequency of 7.1% (≈12/168). In some embodiments, the preselected frequency criteria are satisfied when each synergy state event of the one or more synergy state events has a relative frequency higher than a relative frequency of any other state events that have transitions to the target state event (e.g., top two state events with highest relative frequencies). In some embodiments, the preselected frequency criteria are satisfied when each synergy state event of the one or more synergy state events has a relative frequency higher than a preselected threshold (e.g., more than 10%).

In some embodiments, a synergy effect of a respective synergy state event is determined. In some embodiments, the synergy effect of the respective synergy state event is determined at least based on the relative frequency of the respective synergy state event. In some embodiments, the synergy effect of the respective synergy state event is determined also based on a degree of progress in achieving the respective synergy state event. For example, the synergy effect of the respective synergy state event is based on a multiple of the relative frequency of the respective synergy state event and the degree of progress in achieving the respective synergy state event.

In some embodiments, the system determines (520) a probability of achieving the target state from the current state of the user. In some embodiments, the probability of achieving the target state from the current state of the user is based on synergy effects of the user's existing goals and/or recommended goals. In some embodiments, the probability of achieving the target state from the current state of the user is also based on a degree of progress in achieving the target state event. In some embodiments, the probability of achieving the target state from the current state of the user is set to be no less than 50%.

In some embodiments, the system determines (522) the probability of achieving the target state from the current state of the user based on relative frequencies of the one or more synergy events.

In some embodiments, subsequent to storing the state events and the causality in the database, the system receives (524, FIG. 5C) a second request to recommend one or more target states. In response to receiving the second request, the system obtains the current state of the user. The current state of the user includes one or more state events associated with the user. The system determines one or more target states based on the current state of the user and the state events and the causality stored in the database, including identifying one or more probable state events. Each probable state event of the one or more probable state events has a causality value from the current state of the user that satisfies second preselected causality criteria. The system provides at least a subset of the one or more target states. For example, as shown in FIG. 4D, for a person having achieved goal 3, goal 5 is identified as a probable state event, because a number of transitions from goal 3 to goal 5 is high. In some cases, goal 1 is also identified as a probable state event, because once the person achieves goal 5, the person is likely to achieve goal 1. In some embodiments, the second preselected causality criteria are deemed to be satisfied in accordance with a determination that the causality value exceeds a preselected threshold. In some embodiments, the second preselected causality criteria are deemed to be satisfied in accordance with a determination that the causality value is higher than a causality value for any other transition from the current state.

In some embodiments, the one or more probable state events are (526) one or more M-generation probable state events. For example, in FIG. 4D, goal 5 is an M generation probable state event (e.g., first generation). The system repeats identifying one or more probable state events so that one or more M+1 generation probable state events are identified for at least one M generation probable state event (e.g., goal 1 is generated as a second generation probable state event). Each M+1 generation probable state event has a causality value for the one M generation probable state event that satisfies the second preselected causality criteria. M is advanced by a generation each time the identifying is repeated (e.g., after identifying a second generation probable state event, a third generation probable state event is identified).

In some embodiments, subsequent to storing the state events and the causality in the database, the system receives (528, FIG. 5D) a third request to identify one or more users. In response to receiving the third request, the system identifies one or more target state events of the user, and identifies one or more candidate users who are distinct from the user. Each candidate user of the one or more candidate users is associated with at least one target state event of the one or more target state events associated with the user. The system identifies at least a subset of the one or more candidate users based on preselected user selection criteria, and provides at least the subset of the one or more candidate users identified based on the preselected user selection criteria. For examples, as shown in FIG. 4E, persons who have the same goals as the user (e.g., user 1) are identified as candidate users. Based on the progress each person has made on those goals, one or more persons are recommended.

In some embodiments, the preselected user selection criteria require (530) that a probability of achieving a target state event, of the one or more target state events of the user, for a candidate user is higher than a probability of achieving the target state event for any other candidate user of the one or more candidate users. For example, as shown in FIG. 4F, for user 1 who wants to achieve goal 3, user 4 is identified because user 4 has the highest probability of (or the most progress in) achieving goal 3. Thus, user 4 can be recommended as a mentor to user 1 in achieving goal 3. In some embodiments, a probability of achieving the target state event is determined based on a degree of progress in achieving the target state event. In some embodiments, the degree of progress in achieving the target state event is deemed to be the probability of achieving the target state event.

In some embodiments, the preselected user selection criteria require (532) that a sum of respective probabilities of achieving respective target state events, of the one or more target state events of the user, for a candidate user is higher than a sum of respective probabilities of achieving respective target state events for any other candidate user of the one or more candidate users. For example, as shown in FIG. 4F, for user 1, user 4 is identified because user 4 has the highest sum of probabilities of achieving the target state events. Thus, user 4 can be recommended as a mentor to user 1 in achieving the target state events.

In some embodiments, the preselected user selection criteria require (534) that all of the one or more target state events of the user are associated with a candidate user as target state events of the candidate user. For example, as shown in FIG. 4F, a candidate user (e.g., user 2) has all of the target state events of user 1 (e.g., goal 1 through goal 7) as the candidate user's target state events, and user 2 is recommended as a potential friend to user 1 for having common goals.

In some embodiments, the preselected user selection criteria require that a predefined number of the one or more target state events of the user are associated with a candidate user as target state events of the candidate user.

In some embodiments, the preselected user selection criteria require (536) that a sum of respective probabilities of achieving respective target state events, of the one or more target state events of the user, by a candidate user is closer to a sum of respective probabilities of achieving the respective target state events by the user than any other candidate user of the one or more candidate users. For example, as shown in FIG. 4E, for user 1, user 5 is identified because the sum of probabilities of achieving the target state events for user 5 is the closest to the sum of probabilities of achieving the target state events for user 1.

In some embodiments, subsequent to storing the state events and the causality in the database, the system receives (538, FIG. 5E) a fourth request to recommend one or more target state events. In response to receiving the fourth request, the system identifies one or more state events of the user and identifies a plurality of related users. Each related user has at least one state event of the one or more state events of the user. The system identifies one or more recommended state events of the plurality of related users. Each recommended state event of the one or more recommended state events is not associated with the user. The system identifies at least a subset of the one or more recommended state events of the plurality of related users based on preselected recommended state event criteria, and provides at least the subset of the one or more recommended state events of the plurality of related users. For example, as shown in FIG. 4A, based on the goal of user 1 (e.g., goal 1), users who also have goal 1 are identified. Then, other goals of the identified users are identified and a most frequent goal that user 1 does not have (e.g., goal 2) is recommend to user 1. In a more specific example, for a user 1 who has a goal of receiving a degree in computer science from a particular school, the system identifies other users who also want to receive, or have received, a degree in computer science from the particular school, identify goals of the identified users, and recommend popular goals to user 1.

In some embodiments, subsequent to storing the state events and the causality in the database, the system receives (540) a fifth request to identify one or more past states; and, in response to receiving the fifth request, obtains the current state of the user. The current state of the user includes one or more state events associated with the user. The system determines one or more past states based on the current state of the user and the state events and the causality stored in the database, including identifying one or more probable past state events. Each probable past state event of the one or more probable past state events has a causality value to the current state of the user that satisfies third preselected causality criteria. The system provides at least a subset of the one or more past states. For example, as shown in FIG. 4B, when the user 1 has achieved goal 1, the most likely cause state event (e.g., goal 5) is identified as a past event, because the transition from goal 5 to goal 1 has a highest occurrence among all possible transitions to goal 1. In some embodiments, the third preselected causality criteria are deemed to be satisfied in accordance with a determination that the causality value exceeds a preset threshold. In some embodiments, the third preselected causality criteria are deemed to be satisfied in accordance with a determination that the causality value is more than a causality value for a transition from any other state event to the current state.

In some embodiments, the one or more probable past state events are (542) one or more P-generation probable past state events. For example, goal 5 is identified as a −1 generation probable past state event. The system repeats identifying one or more probable past state events so that one or more P−1 generation probable past state events are identified for at least one P generation probable past state event. For example, goal 3 is identified as a −2 generation probable past state event, because the transition from goal 3 to goal 5 has a highest occurrence among all possible transitions to goal 5. Each P−1 generation probable past state event has a causality value to the one P generation probable past state event that satisfies the third preselected causality criteria and P is reduced by a generation each time the identifying is repeated.

In some embodiments, the system receives multiple requests concurrently and respond to the multiple requests concurrently. For example, the system receives tens of requests, retrieves information from the database, processes the requests, and provides results.

In some embodiments, a respective request (e.g., the first request, the second request, the third request, the fourth request, the fifth request, etc.) is transmitted as an electrical signal or an optical signal.

In some embodiments, some of the operations described herein are performed independent of a human intervention. For example, calculations and determinations are made without a manual input of a user (other than initiating a request).

The foregoing description, for purpose of explanation, has been described with reference to specific embodiments. However, the illustrative discussions above are not intended to be exhaustive or to limit the scope of claims to the precise forms disclosed. Many modifications and variations are possible in view of the above teachings. The embodiments were chosen and described in order to best explain the underlying principles and their practical applications, to thereby enable others skilled in the art to best utilize the described principles and various embodiments with various modifications as are suited to the particular use contemplated.

What is claimed is:

1. A method, comprising:
at a computer system with one or more processors and memory:
crawling a plurality of web pages, a respective web page containing biographical information of a respective person;
parsing the crawled information into state events and determining causality between any two of the state events;
storing the state events and the causality in a database;
subsequent to storing the state events and the causality in the database, receiving a first request from a user to determine a path to a target state, wherein the target state includes a target state event; and,
in response to receiving the first request:
obtaining a current state of the user, wherein the current state of the user includes one or more state events associated with the user;
determining one or more paths from the current state of the user to the target state based on the current state of the user and the state events and the causality stored in the database, including identifying one or more recommended state events, each recommended state event of the one or more recommended state events having a causality value for the target state that satisfies first preselected causality criteria; and
providing at least one path from the current state of the user to the target state, wherein:
the one or more recommended state events are one or more N-generation recommended state events; and
the method includes repeating identifying one or more recommended state events so that one or more N−1 generation recommended state events are identified for at least one N generation recommended state event, wherein each N−1 generation recommended state event has a causality value for the one N generation recommended state event that satisfies the first preselected causality criteria and N is reduced by a generation each time the identifying is repeated.

2. The method of claim 1, including:
identifying one or more synergy state events, wherein each synergy state event of the one or more synergy state events has a relative frequency that satisfies preselected frequency criteria, and the relative frequency is based on respective frequencies of transitions to the target state event from multiple state events, that have transitions to the target state event, including the synergy state event.

3. The method of claim 1, including:
determining a probability of achieving the target state from the current state of the user.

4. The method of claim 3, including determining the probability of achieving the target state from the current state of the user based on relative frequencies of the one or more synergy events.

5. The method of claim 1, including:
subsequent to storing the state events and the causality in the database, receiving a second request to recommend one or more target states; and,
in response to receiving the second request:
obtaining the current state of the user, wherein the current state of the user includes one or more state events associated with the user;
determining one or more target states based on the current state of the user and the state events and the causality stored in the database, including identifying one or more probable state events, each probable state event of the one or more probable state events having a causality value from the current state of the user that satisfies second preselected causality criteria; and
providing at least a subset of the one or more target states.

6. The method of claim 5, wherein:
the one or more probable state events are one or more M-generation probable state events; and
the method includes repeating identifying one or more probable state events so that one or more M+1 generation probable state events are identified for at least one M generation probable state event, wherein each M+1 generation probable state event has a causality value for the one M generation probable state event that satisfies the second preselected causality criteria and M is advanced by a generation each time the identifying is repeated.

7. The method of claim 1, including:
subsequent to storing the state events and the causality in the database, receiving a third request to identify one or more users; and,
in response to receiving the third request:
identifying one or more target state events of the user;
identifying one or more candidate users who are distinct from the user, wherein each candidate user of the one or more candidate users is associated with at least one target state event of the one or more target state events associated with the user;
identifying at least a subset of the one or more candidate users based on preselected user selection criteria; and
providing at least the subset of the one or more candidate users identified based on the preselected user selection criteria.

8. The method of claim 7, wherein the preselected user selection criteria require that a probability of achieving a target state event, of the one or more target state events of the user, for a candidate user is higher than a probability of achieving the target state event for any other candidate user of the one or more candidate users.

9. The method of claim 7, wherein the preselected user selection criteria require that a sum of respective probabilities of achieving respective target state events, of the one or more target state events of the user, for a candidate user is higher than a sum of respective probabilities of achieving respective target state events for any other candidate user of the one or more candidate users.

10. The method of claim 7, wherein the preselected user selection criteria require that all of the one or more target state events of the user are associated with a candidate user as target state events of the candidate user.

11. The method of claim 7, wherein the preselected user selection criteria require that a sum of respective probabilities of achieving respective target state events, of the one or more target state events of the user, by a candidate user is closer to a sum of respective probabilities of achieving the respective target state events by the user than any other candidate user of the one or more candidate users.

12. The method of claim 1, including:
subsequent to storing the state events and the causality in the database, receiving a fourth request to recommend one or more target state events; and,
in response to receiving the fourth request:
identifying one or more state events of the user;
identifying a plurality of related users, wherein each related user has at least one state event of the one or more state events of the user;
identifying one or more recommended state events of the plurality of related users, wherein each recommended state event of the one or more recommended state events is not associated with the user;
identifying at least a subset of the one or more recommended state events of the plurality of related users based on preselected recommended state event criteria; and
providing at least the subset of the one or more recommended state events of the plurality of related users.

13. The method of claim 1, including:
subsequent to storing the state events and the causality in the database, receiving a fifth request to identify one or more past states; and,
in response to receiving the fifth request:
obtaining the current state of the user, wherein the current state of the user includes one or more state events associated with the user;
determining one or more past states based on the current state of the user and the state events and the causality stored in the database, including identifying one or more probable past state events, each probable past state event of the one or more probable past state events having a causality value to the current state of the user that satisfies third preselected causality criteria; and
providing at least a subset of the one or more past states.

14. The method of claim 13, wherein:
the one or more probable past state events are one or more P-generation probable past state events; and
the method includes repeating identifying one or more probable past state events so that one or more P−1 generation probable past state events are identified for at least one P generation probable past state event, wherein each P−1 generation probable past state event has a causality value to the one P generation probable past state event that satisfies the third preselected causality criteria and P is reduced by a generation each time the identifying is repeated.

15. A computer system, comprising:
one or more processors; and
memory storing one or more programs for execution by the one or more processors, the one or more programs including instructions for:
crawling a plurality of web pages, a respective web page containing biographical information of a respective person;
parsing the crawled information into state events and determining causality between any two of the state events;
storing the state events and the causality in a database;

subsequent to storing the state events and the causality in the database, receiving a first request from a user to determine a path to a target state, wherein the target state includes a target state event; and, in response to receiving the first request:

obtaining a current state of the user, wherein the current state of the user includes one or more state events associated with the user;

determining one or more paths from the current state of the user to the target state based on the current state of the user and the state events and the causality stored in the database, including identifying one or more recommended state events, each recommended state event of the one or more recommended state events having a causality value for the target state that satisfies first preselected causality criteria; and providing at least one path from the current state of the user to the target state, wherein:

the one or more recommended state events are one or more N-generation recommended state events; and the one or more programs include instructions for repeating identifying one or more recommended state events so that one or more N−1 generation recommended state events are identified for at least one N generation recommended state event, wherein each N−1 generation recommended state event has a causality value for the one N generation recommended state event that satisfies the first preselected causality criteria and N is reduced by a generation each time the identifying is repeated.

16. A non-transitory computer readable storage medium, storing:

one or more programs for execution by one or more processors of a computer system, the one or more programs including instructions for:

crawling a plurality of web pages, a respective web page containing biographical information of a respective person;

parsing the crawled information into state events and determining causality between any two of the state events;

storing the state events and the causality in a database;

subsequent to storing the state events and the causality in the database, receiving a first request from a user to determine a path to a target state, wherein the target state includes a target state event; and, in response to receiving the first request:

obtaining a current state of the user, wherein the current state of the user includes one or more state events associated with the user;

determining one or more paths from the current state of the user to the target state based on the current state of the user and the state events and the causality stored in the database, including identifying one or more recommended state events, each recommended state event of the one or more recommended state events having a causality value for the target state that satisfies first preselected causality criteria; and providing at least one path from the current state of the user to the target state, wherein:

the one or more recommended state events are one or more N-generation recommended state events; and the one or more programs include instructions for repeating identifying one or more recommended state events so that one or more N−1 generation recommended state events are identified for at least one N generation recommended state event, wherein each N−1 generation recommended state event has a causality value for the one N generation recommended state event that satisfies the first preselected causality criteria and N is reduced by a generation each time the identifying is repeated.

* * * * *